(12) United States Patent
Tsai et al.

(10) Patent No.: US 6,506,340 B1
(45) Date of Patent: Jan. 14, 2003

(54) ANTIFOAMING DEVICE AND METHOD FOR EXTRACORPOREAL BLOOD PROCESSING

(75) Inventors: Chi-Chun Tsai, Lawrenceville, GA (US); Robert E Haynes, Lakewood, CO (US)

(73) Assignee: Cobe Cardiovascular, Inc., Arvada, CO (US)

( * ) Notice: Subject to any disclaimer, the term of this patent is extended or adjusted under 35 U.S.C. 154(b) by 0 days.

(21) Appl. No.: 08/069,867

(22) Filed: Jun. 1, 1993

(51) Int. Cl.$^7$ .......................... A61M 1/36; A61M 37/00
(52) U.S. Cl. .......................... 422/45; 422/44; 604/4.01; 604/6.14; 128/DIG. 3; 261/DIG. 28
(58) Field of Search .............. 604/4–6.14, 122; 128/898, DIG. 3; 422/44, 48, 45, 46, 47; 55/16, 158; 210/646, 321.81, 321.9, 500.23, 500.24; 261/DIG. 28; 427/235, 372.2

(56) References Cited

U.S. PATENT DOCUMENTS

| | | | |
|---|---|---|---|
| 4,190,563 A | * | 2/1980 | Bosley et al. ............... 604/368 |
| 4,203,945 A | | 5/1980 | De Wall |
| 4,214,020 A | | 7/1980 | Ward et al. |
| 4,448,188 A | | 5/1984 | Loeb |
| 4,540,407 A | * | 9/1985 | Dunn .......................... 2/161.7 |
| 4,704,203 A | | 11/1987 | Reed |
| 5,059,342 A | | 10/1991 | Blease |
| 5,160,332 A | | 11/1992 | Nomura ...................... 604/405 |
| 5,162,102 A | * | 11/1992 | Nogawa et al. ......... 128/DIG. 3 |
| 5,202,242 A | | 4/1993 | Mynderse et al. |
| 5,211,913 A | * | 5/1993 | Hagiwara et al. ........... 422/102 |
| 5,221,474 A | | 6/1993 | Yokono et al. |
| 5,232,828 A | * | 8/1993 | Phi-Wilson et al. ........ 422/102 |
| 5,277,820 A | | 1/1994 | Ash |
| 5,429,802 A | | 7/1995 | Hagiwara et al. |
| 5,438,041 A | | 8/1995 | Zheng et al. |
| 5,474,740 A | | 12/1995 | Trudell et al. |
| 5,536,884 A | | 7/1996 | Stoeckigt et al. |
| 5,540,653 A | | 7/1996 | Schock et al. |
| 5,558,834 A | | 9/1996 | Chu et al. |
| 5,863,501 A | | 1/1999 | Cosentino |

FOREIGN PATENT DOCUMENTS

| | | |
|---|---|---|
| EP | 0 068 509 | 1/1983 |
| EP | 0214614 | * 3/1987 |
| EP | 0323341 | 12/1988 |
| EP | 0323341 | * 7/1989 |
| GB | 1 426 668 | 3/1976 |
| JP | 62-5173 | 1/1983 |
| JP | 59-37320 | 4/1983 |
| JP | 62-43565 | 4/1984 |
| JP | 2-124170 | 5/1990 |
| JP | 4-345694 | 12/1992 |
| WO | 92/21387 | 12/1992 |

OTHER PUBLICATIONS

Glenville et al., "Preliminary Communications: Coronary artery surgery with patient's lungs as oxygenator," *The Lancet*, 328(8514):1005–1006 (1986).

Nishida et al., "Clinical experience of assisted circulation with a centrifugal pump at Tokyo Women's Medical College," *Artif. Organs*, 17(7):625–629 (Abstract) (1993).

Reed et al., "Cardiopulmonary Perfusion," Texas Medical Press, Inc., Houston, TX, p. 294 (1975).

*ICI product literature.*
*BASF product literature (1989).*
*Dow Corning product literature (1985).*

(List continued on next page.)

*Primary Examiner*—Angela D. Sykes
*Assistant Examiner*—Patricia Bianco
(74) *Attorney, Agent, or Firm*—Popovich & Wiles, P.A.

(57) ABSTRACT

A medical instrument and method is provided for defoaming or preventing formation of foam in blood during extracorporeal blood circulation. The method comprises durably coating hydrophobic blood-contact surfaces with a nontoxic, biocompatible surface-active defoaming agent.

12 Claims, 1 Drawing Sheet

OTHER PUBLICATIONS

J.M. Orenstein, et al. (1982), *"Microemboli Observed in Deaths Following Cardiopulmonary Bypass Surgery,"* Human Pathology 13:1082–1090.

E. S. Wright et al. (1963), *"Fat Globulemia in Extracorporeal Circulation,"* Surgery 53:500–504.

Y. Miyauchi et al. (1966), *"Adjunctive Use of a SurfaceActive Agent in Extracorporeal Circulation,"* 33 & 34, I–71–I–77.

C. Roze (1966), *"Osmotic Behavior of Erythrocytes in Solutions of a Non–ionic Detergent: Pluronic F–68,"* C. R. Acad. Sci. 263:1615–1618.

A. C. Hymes and P. Baute (1964), *"Pluronics: First Use as a Plasma Expander,"* Supplement II to Circulation 35 & 36, II–148.

A. C. Hymes et al. (1968), *"A comparison of Pluronic F–68, low molecular weight dextran, mannitol, and saline as priming agents in the heart–lung apparatus,"* J. Thoracic and Cardiovas. Surg. 56:16–22.

Lee, et al. (1989), *"Protein–resistant Surfaces Prepared by PEO–containing Block Copolymer Surfactants,"* J. Biomedical Material Research 23:351–368.

M. Amjii and K. Park (1992), *"Prevention of Protein Adsorption and Platelet Adhesion on Surfaces by PEO/PPO/PEO Triblock Copolymers,"* Biomaterial 13:682–692.

*BASF product literature (1991).*

*Cobe Laboratories, Inc., Product History and Materials.*

Schmolka, I.R., *"Polyalkylene Oxide Block Copolymers,"* Nonionic Surfactants, Chapter 10, pp. 300–371 (1967).

Owen, M.J., *"Antifoaming Agents,"* Antibodies and Antigens, Polymer–Bound, vol. 2, pp. 59–72.

BASF Technical Bulletin, *"Plurafac RA–20 Linear Alcohol Alkoxylate,"* (1987).

BASF Technical Bulletin, *"Plurafac RA–30 Linear Alcohol Alkoxylate,"* (1987).

Bryon, K.J., *"Defoaming agents,"* Critical Reports on Applied Chemistry, *"Recent Developments in the Technology of Surfactants,"* (M.R. Porter, Ed., Elsevier Applied Science, London and New York)(1990) 30:133–161.

Lundsted, L.G. and Schmolka, I.R., *"The Synthesis and Properties of Block Copolymer Polyol Surfactants"*, Block and Graft Copolymerization, pp. 1–111.

BASF Product Literature, Pluronic & Tetronic Block Copolymer Surfactants, 1989.*

BASF Performance Chemicals literature, 1991.*

* cited by examiner

ANTIFOAMING DEVICE AND METHOD FOR EXTRACORPOREAL BLOOD PROCESSING

FIELD OF THE INVENTION

This invention is in the field of medical devices, specifically defoaming components for extracorporeal blood processing devices such as oxygenators and cardiotomy reservoirs.

BACKGROUND OF THE INVENTION

Blood processing apparatus including oxygenators, cardiotomy reservoirs and defoamers, blood filters, autotransfusion devices, drip chambers, and other devices through which blood is moved, e.g., by pumping, often require agitation such that air is mixed with blood, causing foaming. This foam must be removed before the blood is put into the patient's circulatory system.

Many surfactants are used as industrial antifoaming agents including selected block copolymer polyol surfactants, polyether block copolymers, polyoxyethylene sorbitan esters and silicone-based surfactants. These surfactants are generally used as defoamers by mixing them into the liquid to be defoamed.

TWEEN 80™ (ICI Specialty Chemicals, see ICI product literature) is a well-known industrial and biological surfactant which is a polyoxyethylene sorbitan ester. TWEEN 80™ has been used as a debubbling agent in blood-containing medical devices.

Block copolymer polyol surfactants composed of ethylene oxide and propylene oxide are used as defoamers and antifoamers in a wide variety of applications such as industrial processing, latex paints, cleaning, water treatment and fermentation. Currently two groups of polyol surfactants are commercially available. These are PLURONIC™, PLURONIC-R™, TETRONIC™, TETRONIC-R™ and PLUROFAC™ surfactants (BASF product literature 1989). Polyols with various structures and molecular lengths can be synthesized by altering the reaction sequences and degree of polymerization with or without adding ethylenediamine coupling agent. Block copolymers composed of ethylene oxide are hydrophilic while those composed of propylene oxide are hydrophobic. These polyol surfactants have not been known to be applied as defoamers/antifoamers in blood-contacting medical devices especially for use in extracorporeal circulation.

ANTIFOAM A™, Dow Corning Corporation, Midland, Mich. (Dow Corning Product Literature, 1985), a polydimethylsiloxane surfactant, has been used as an antifoaming agent for blood processing devices. Dow Corning also manufactures a similar polydimethylsiloxane defoaming agent sold under the trademark SIMETHICONE™ which may be used in blood processing devices. ANTIFOAM A™ is coated on blood-contact surfaces of such devices to prevent foaming. Device surfaces are usually coated by dipping them in a solution of ANTIFOAM A™ in a halogenated hydrocarbon. Generally, defoaming units of blood processing devices provide a very large surface area which is covered by the defoaming agent. The surface area is usually composed of a synthetic material such as polyurethane foam, polypropylene mesh, polyvinylchloride strips or stainless steel wool. Other surfactants containing silicone which are water-soluble are also known to the art including those of GE Silicone Division, Waterford, N.Y. such as SM-70.

Silicone-containing surfactants used in blood processing devices, specifically, ANTIFOAM A™, have recently been implicated in the formation of emboli in patients who died after cardiopulmonary bypass surgery. (J. M. Orenstein, et al. (1982), "Microemboli Observed in Deaths Following Cardiopulmonary Bypass Surgery," Human Pathology 13:1082–1090.) ANTIFOAM A™, as a hydrophobic surfactant, has the further disadvantage of retarding liquids in the defoaming unit of oxygenating instruments, thus unnecessarily impeding blood flow through the unit.

To avoid problems of blood interaction with the blood-contact surfaces which may cause trauma to the blood, the use of defoaming agents has been described in combination with heparin in blood processing devices. (L-C. Hsu, et al., "Thrombo-resistant Coating for Defoaming Applications," PCT Publication WO 92/21387.) Defoaming agents are described as comprised of both active compounds and carriers, occasionally including a spreading agent. Typical active compounds listed include fatty acid amides, higher molecular weight polyglycols, fatty acid esters, fatty acid ester amides, polyalkene glycols, organophosphates, metallic soaps of fatty acids, silicone oils, hydrophobic silica, organic polymers, saturated and unsaturated fatty acids, and higher alcohols. Typical carriers include paraffinic, naphthenic, aromatic, chlorinated, or oxygenated organic solvents. ANTIFOAM A™ dissolved in a mixture of FREON (DuPont Co.) and methylene chloride in combination with heparin is a preferred antifoaming composition in this patent application for avoiding problems of blood interaction with blood-contact surfaces.

Nogawa, et al. U.S. Pat. No. 5,162,102 describes the use of nonionic surface-active agents which are polyethers consisting of block copolymers of propylene oxide and ethylene oxide (i.e., PLURONIC™ and TETRONIC™ surfactants), to coat blood-contacting surfaces of medical devices for debubbling purposes. In that patent a debubbling agent is used to coat the hydrophobic blood-contact surfaces so that air can be removed from the system during a priming operation prior to blood circulation, leaving few bubbles adhered to the surfaces, as the patent teaches that during blood circulation, such bubbles gradually enter the blood, causing blood foaming. The surfactant may be used by coating on the inside of the housing. Then when the priming liquid is passed into the system, the surfactant dissolves and is distributed over the entirety of the blood-contact surfaces, and renders them more hydrophilic. In the preferred embodiment disclosed in this patent, a "debubbler" or defoaming unit to remove bubbles from blood is described. This defoaming unit (such as a urethane, cellulose, or nylon foam), works to remove bubbles from blood by allowing bubbles to grow by virtue of its hydrophobic nature. Thus, this patent teaches away from the use of a surfactant durably deposited onto the blood-contact surfaces, particularly onto defoamer surfaces, as such would interfere with the function of the defoamer described in said patent. The PLURONIC F68 debubbling composition disclosed in U.S. Pat. No. 5,162,102 is not suitable as a defoaming composition as defined herein. As set forth in the BASF product literature (1989), page 13, F68 is a water-soluble surfactant that produces foam and should only be used in applications where foam production is desirable.

A number of water soluble PLURONIC™ or TETRONIC™ surfactants have been found to produce fair to excellent results when used in combination with buffers and osmolality fillers as debubbling agents for sheath streams in biomedical analytical systems. These are PLURONIC P85™, P84, P105, P87 and TETRONIC 908™.

European Patent Publication 0 214 614 published Mar. 18, 1987, for "Non-Lytic Sheath Composition." The water solubility of these surfactants at operating temperatures would preclude their use in defoaming applications where durable retention on a hydrophobic surface is desired.

The nonbiotoxic nature of polyol surfactants was known about thirty years ago. Generally the polyols have low acute oral and dermal toxicity and low potential for causing irritation or sensitization. The typical oral LD50™ is greater than 10 grams per kilogram and dermal LD50™ is greater than five grams per kilogram. In medical applications, the PLURONIC F68™ polyol has been extensively studied. Adding F68 to blood to minimize fat globulemia during cardiopulmonary bypass surgery was corroborated on clinical patients. (E. S. Wright et al. (1963), Fat Globulemia in Extracorporeal Circulation,"Surgery 53:500–504; and Y. Miyauchi et al. (1966),"Adjunctive Use of a Surface-Active Agent in Extracorporeal Circulation," Supplement I to Circulation, 33 & 34, I-71–1-77.) Concentrations less than five percent F68 were shown to protect erythrocytes against osmotic hemolysis. (C. Roze (1966), "Osmotic Behavior of Erythrocytes in Solutions of a Non-ionic Detergent: Pluronic F-68," C.R. Acad. Sci. 263:1615–1618.) The use of F68 as a blood plasma expander in heart-lung bypass has been suggested. (A. C. Hymes and P. Baute (1964), "Pluronics: First Use as a Plasma Expander," Supplement II to Circulation 35 & 36, II-148; A. C. Hymes et al. (1968), "A comparison of Pluronic F-68, low molecular weight dextran, mannitol, and saline as priming agents in the heart-lung apparatus," J. Thoracic and Cardiovas. Surg. 56:16–22.)

Other workers have looked at the biocompatibility of PLURONIC™ surfactants. Lee, et al. (1989), "Protein-resistant Surfaces Prepared by PEO-containing Block Copolymer Surfactants," J. Biomedical Material Research 23:351–368, incorporated herein by reference, discloses the coating of low density polyethylene film with polyethylene oxide (PEO) and polybutylene oxide (PBO) block copolymers including PLURONIC L64™ (BASF), SYNPERONIC PE-L64C™ (ICI), TETRONIC 1504™ (BASF) and BUTRONIC 184™ (BASF). Adsorption of the block copolymers on the surface depended on the molecular structure of the copolymers and protein resistance was dependent on the amount of copolymer adsorbed and on PEO chain mobility.

M. Amjii and K. Park (1992), "Prevention of Protein Adsorption and Platelet Adhesion on Surfaces by PEO/PPO/PEO Triblock Copolymers," Biomaterial 13:682–692, incorporated herein by reference, discloses that the ability of PLURONIC™ to prevent platelet adhesion was mainly dependent on the number of propylene oxide residues (rather than the number of ethylene oxide residues). The number of propylene oxide residues in the copolymer is also linked to the tightness of binding to a hydrophobic substrate. PLURONIC™ surfactants tested included L63, L64, P65, F68, P103, P104, P105 and P105. PLURONIC P103™ and P108 were said to be effective in repelling fibrinogen and platelets from surfaces. As long as the surfactant is tightly bound to the surface, which binding is determined by the number of propylene oxide residues, then the PEO moieties can effectively block fibrinogen adsorption and platelet adhesion by steric repulsion.

To solve the problems of embolus formation, blood interaction with blood-contact surfaces, retention of fluid in defoaming units, and the environmentally unsafe use of halogenated hydrocarbons as solvents, it is desirable to provide an antifoaming composition which is biocompatible, long-lasting when coated on the blood-contact surfaces, i.e. does not wash off into the blood, and which may be solubilized in an alcohol or nonhalogenated hydrocarbon solvents.

SUMMARY OF THE INVENTION

Figure 1:
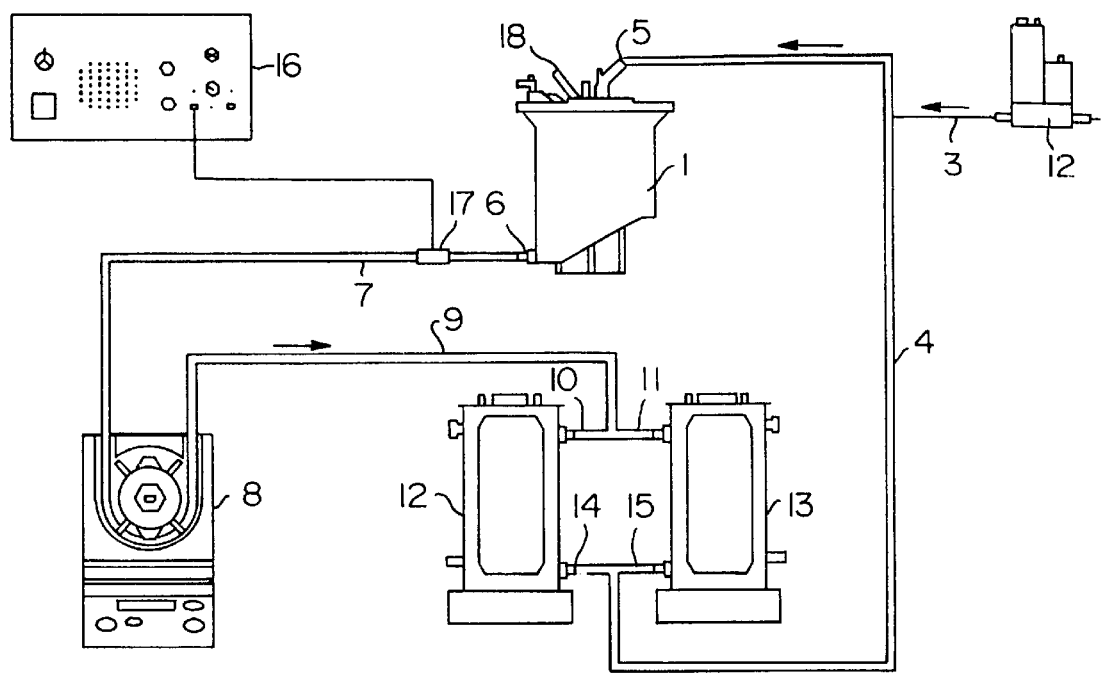
FIG. 1 shows apparatus used in the blood defoaming assay method used in this invention.

A medical instrument is provided comprising a blood-contact surface formed of a hydrophobic material and having a nontoxic, biocompatible surface-active defoaming agent durably deposited onto said blood-contact surface, wherein said surface-active agent has a blood defoaming screen test filter bypass foam grade of 2 or less.

A method of fabricating a medical instrument is also provided comprising the steps of:

(a) assembling a medical instrument having a blood-contact surface formed of a hydrophobic material;

(b) coating at least a portion of said blood-contact surface with a nontoxic, biocompatible surface-active defoaming agent wherein said surface-active defoaming agent has a blood defoaming screen test filter bypass foam grade of 2 or less;

(c) drying said surface-active agent to durably deposit said surface active agent onto said blood-contact surface.

A method of defoaming or preventing foam formation in blood is also provided comprising contacting said blood with a hydrophobic material coated with a nontoxic, biocompatible surface-active defoaming agent durably deposited onto said hydrophobic material, wherein said surface-active agent has a blood defoaming screen test filter bypass foam grade of 2 or less.

Said medical instrument may be a defoamer, oxygenator, heat exchanger, cardiotomy reservoir, blood filter, autotransfusion device, blood line, or other such instrument requiring movement of blood, e.g., by pumping. Preferably said medical instrument is a membrane oxygenator system comprising a filter/defoamer reservoir unit such as the Cobe CML oxygenator system comprising the Cobe HVRF-3700 (Cobe Laboratories, Inc., Lakewood, Col.) defoamer and reservoir. More preferably, said medical instrument is the defoaming unit portion of such reservoir.

Blood-contact surfaces include materials made of hydrophobic polymeric materials such as polypropylene, polyethylene, polysulfone, polyacrylonitrile, polytetrafluoroethylene and cellulose acetate, polycarbonate, acrylstyrene copolymers and other hydrophobic polymeric materials.

Surface-active agents (also called surfactants) which are nontoxic are those for which the oral LD50 is greater than about five grams per kilogram and the dermal LD50 is greater than about five grams per kilogram, or those listed by the manufacturers as suitable for food or pharmaceutical uses.

Biocompatible surface active agents are those which are nontoxic and which resist protein absorption and platelet adhesion. Suitable assays for measurement of the latter factors are set forth, e.g., in M. Amjii and K. Park (1992), "Prevention of Protein Adsorption and Platelet Adhesion on Surfaces by PEO/PPO/PEO Triblock Copolymers," Biomaterial 13:682–692, incorporated herein by reference. To be biocompatible, the surfactant should not increase the protein absorption over uncoated blood-contact surfaces, and should not cause significant, i.e., less than about 5%, hemolysis.

Durable deposit of the surface active agent on the blood-contact surface means that the surface active agent will not significantly wash off into the bloodstream over the 2–3 hour period of use required for a typical cardiopulmonary bypass operation. Thus, these agents should not be significantly water soluble. Surfactants having a hydrophilic-lipophilic balance (HLB) rating of about 7 or less are thus considered to provide durable deposit on the blood-contact surface. Cloud point is also correlated with solubility in blood. Surfactants having a cloud point temperature less than the temperature at which the device will be used, i.e., less than about 37° C., and more preferably less than about 20° C., are therefore also considered to provide durable deposit on the blood-contact surface.

The surface-active agent is preferably also one which renders the blood-contact surface hydrophilic to avoid prolonged retention of blood or priming saline in the defoamer unit. Suitable surface-active agents thus preferably have a breakthrough volume as defined herein of no more than about 50 cc saline as measured according to the protocol set forth in Example 3.

The deposition of the surface-active defoaming agent onto the blood-contact surface may be done by any means known to the art, such as dip-coating, spraying or painting. Preferably deposition is performed by spraying or dip coating or both. The surface-active agent is preferably first dissolved or dispersed in a carrier such as an organic solvent. Preferably said carrier does not contain halogenated hydrocarbons. More preferably, the carrier comprises an alcohol solvent such as ethyl or isopropyl alcohol.

The surface-active defoaming agent is preferably selected from the group consisting of polyethers consisting essentially of block copolymers of propylene oxide and ethylene oxide such as the PLURONIC™ and TETRONIC™ surfactants of BASF, and primary alkoxylated alcohols, such as the PLUROFAC™ surfactants of BASF. Preferably, said surface-active agent is selected from the group consisting of PLURONIC L61™, PLURONIC L81™, PLURONIC L101™, PLURONIC L121™, PLURONIC R 17R1™, PLURONIC R25R1, PLURONIC R 25R2™, PLURONIC R 31R1™, PLURONIC R 31R2, TETRONIC 701, TETRONIC 901, TETRONIC 1101™, TETRONIC 1301™, TETRONIC 1501™, TETRONIC R 50R1™, TETRONIC R 70R1™, TETRONIC 90R1™, TETRONIC R 110R1™, TETRONIC R 130R1™, TETRONIC R 130R2™, TETRONIC R 150R1™, PLUROFAC RA20™, PLUROFAC RA30™, PLUROFAC RA40™ AND PLUROFAC RA43™. More preferably, said surface-active agent is PLURONIC L101™ or PLURONIC R 25R2™.

The defoaming screen test, described in detail below, provides a quick and simple way for the person of ordinary skill in the art to determine the suitability of a particular surfactant for use in this invention. This assay involves pumping bovine blood and air as described below into one of the inlets of the filter/defoamer reservoir unit of a membrane oxygenator system in which blood-contact surfaces of the defoamer have been coated with the surface-active defoaming agent being tested. The amount of foam is measured in the reservoir. A visual measurement of foam height grades visible foam on a scale of 1 to 5, where 1 represents no foam, froth or bubbles in the filter/defoamer unit and 5 represents full surface froth with greater than ⅛" thickness. This number is called the "foam grade" herein, and is preferably measured while blood and air are pumped into the defoamer unit through the filter bypass inlet. The term "blood defoaming screen test filter bypass foam grade" refers to the visual foam rating in the reservoir seen when the blood defoaming screen is run with bovine blood at 6 liters per minute and air at 0.5 liters per minute pumped into the filter bypass inlet of the filter/defoamer reservoir unit. A defoaming screen test blood filter bypass foam grade of 2 or less indicates a surfactant useful in the process of this invention.

DETAILED DESCRIPTION OF THE PREFERRED EMBODIMENTS

A preferred embodiment of this invention provides a membrane oxygenator unit comprising a blood filter/defoamer reservoir unit comprising blood-contact surfaces formed of hydrophobic polymeric materials. These surfaces are coated with a surface-active agent of this invention, preferably by dip-coating in a solution of the surface-active agent, preferably at about 2% concentration in alcohol, preferably ethyl or isopropyl alcohol. The concentration may be less than 2% so long as sufficient surfactant to perform the defoaming function remains on the surface, and of course, may exceed 2% since amounts not adhering to-the surfaces will be washed away during coating or priming.

The surface-active defoaming agents are preferably selected from the group consisting of PLURONIC L61™, PLURONIC L81™, PLURONIC L101™, PLURONIC L121™, PLURONIC R 17R1™, PLURONIC R 25R1™, PLURONIC R 25R2™, PLURONIC R 31R1™, PLURONIC R 31R2™, TETRONIC 701, TETRONIC 901™, TETRONIC 1101™, TETRONIC 1301™, TETRONIC 1501™, TETRONIC R 50R1™, TETRONIC R 70R1™, TETRONIC 90R1™, TETRONIC R 110R1™, TETRONIC R 130R1™, TETRONIC R 130R2™, TETRONIC R 150R1™, PLUROFAC RA20™, PLUROFAC RA30™, PLUROFAC RA40™ AND PLUROFAC RA43™. More preferably, said surface-active agent is PLURONIC L101 ™ or PLURONIC R 25R2™.

Following assembly of the components of the oxygenator, including the defoamer unit, human blood is circulated into said oxygenator through the inlets or ports thereof during surgical procedures, such as cardiopulmonary bypass procedures.

The defoaming unit does not substantially retard the passage of blood therethrough, and resists deposition of blood components thereon.

The surface-active defoaming agents of this invention should have a hydrophilic-lipophilic balance of 7 or less, and should have a cloud point less than the temperature at which the device will be used, i.e. less than about 37° C., and more preferably less than about 20° C. They also preferably provide a breakthrough volume of about 50 cc or less as may be readily determined by one of ordinary skill in the art using the protocol of Example 3. The "breakthrough volume" is the volume of saline which must enter the defoamer unit before the first appearance of saline exiting the defoamer into the reservoir.

In a preferred embodiment of this invention the blood defoaming screen test apparatus is set up as in FIG. 1. Bovine blood, hematocrit about 35, is used to fill filter/defoamer reservoir 1. Air flows into the system from air supply 2 through air line 3 into venous blood line 4, where it mixes with blood and enters through venous inlet 5 into the filter/defoamer reservoir 1. In a more preferred embodiment, blood and air enter the filter bypass inlet 18 of the reservoir rather than the venous inlet. Blood which has passed through the defoamer exits reservoir 1 through reservoir outlet 6 and passes via pump line 7 through pump 8 into pump line 9 which splits into two streams at lines 10 and 11 entering membrane oxygenators 12 and 13, respectively. Blood exits the oxygenators through lines 14 and 15, converging to flow into venous line 4.

A bubble detector 16, preferably a BD100 unit from Hatteland Company, Norway, with a ⅜" probe 17 is preferably set up to take gaseous micro emboli (GME) readings at various points in pump line 7 exiting the filter/defoamer reservoir unit. These readings vary when different test protocols are used, and are useful primarily when used comparatively in evaluating different surfactants under the same test conditions.

Micro emboli are bubbles which are not visually detectable, as opposed to foam which may be seen with the naked eye. Foam is visually measured and the foam grade evaluated in reservoir 1 which is equipped with transparent sides, according to the visual grading scale of Example 1.

Figure 2:
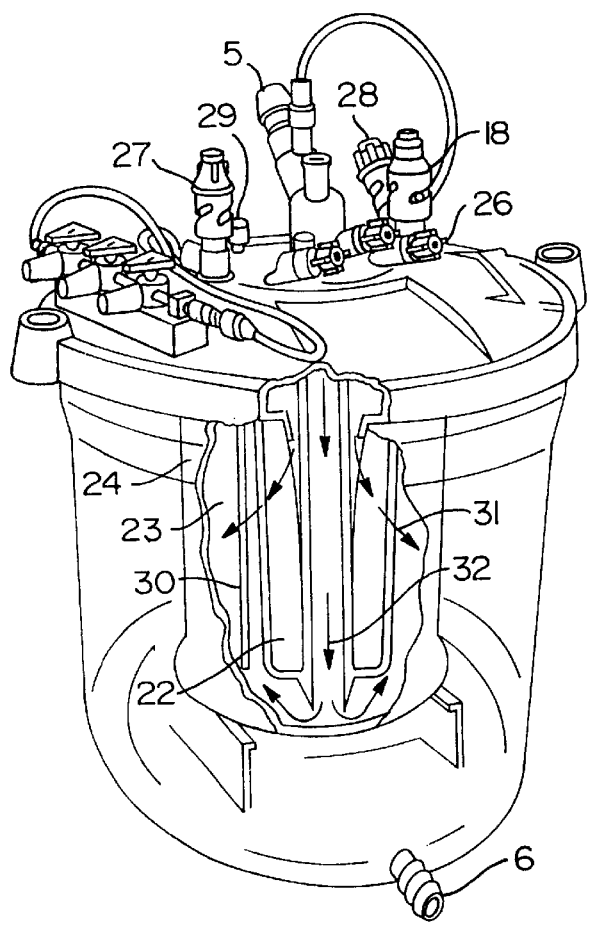
FIG. 2 shows a blood filter/defoamer reservoir suitable for use in this invention by coating with a suitable surface-active agent.

The defoamer portion of the assembly is first dipped in the surfactant being tested, and dried. Alternately, the entire filter/defoamer reservoir may be coated with the surfactant. FIG. 2 shows a filter/defoamer reservoir unit 1 as in FIG. 1, for use in this invention. As described above, during the blood defoaming screen, blood mixed with air is preferably pumped into filter bypass inlet 18. This enables the blood observed in the reservoir to bypass the filter 22, to more directly measure the defoaming capacity of the defoamer comprising air separation netting made of a hydrophobic polymeric material such as polypropylene netting 23 and an outer layer of polyester tricot 24. In other embodiments, blood may enter the reservoir through venous inlet 5 or cardiotomy inlets 26 (a cardiotomy manifold comprising three cardiotomy inlets being depicted in FIG. 2). The unit also comprises a rapid prime inlet 27, a recirculation inlet 28, a fluid administration inlet 29, a fluid administration tube 30, and a reservoir outlet 6. Arrows 31 and 32 indicate cardiotomy and venous blood flow, respectively, when the unit is in normal operation during cardiopulmonary bypass surgery.

EXAMPLES

Example 1

HVR 3700 defoamer units, Cobe Laboratories, Inc., Lakewood, Colo., were each dip-coated with one of the surfactants listed in Table 1. PLURONIC L101™ was solubilized as a 2% (v/v) solution in isopropyl alcohol; ANTIFOAM A™ was solubilized at 2% (v/v) in FREON™ (DuPont Co., Wilmington, Del.); SMA™, a silicone-containing surfactant of Thoratec Laboratories, Inc., was solubilized at 2% (v/v) in acetone; and SM70™, a water-dilutable silicone surfactant of General Electric, Silicones Division, was solubilized at 2% (v/v) in water. An uncoated unit was used as a control. Defoamers were wetted in saline prior to the test. Bovine blood at 35 hematocrit and room temperature was pumped into the venous inlet (also called "port" herein) of the defoamer as shown in FIG. 1 at 6 liters per minute with air at 0.5 liters per minute. The test was continued for five minutes. Foam in the reservoir was visually graded after five minutes, using the following scale:

Visual Grading Scale
1 No foam, froth or bubbles in reservoir
2 Any froth up to ⅓ surface area in the reservoir
3 ⅓ to ⅔ surface area covered with froth in the reservoir
4 Greater than ⅔ surface area covered with froth in the reservoir, but no measurable thickness
5 Full surface froth with measurable thickness (greater than ⅛").

A Hatteland BD100 bubble detector with sensitivity of 5 was set up to probe the line exiting the test unit. Gaseous microemboli (GME) was measured continuously and summed over the test period with results as shown in Table 1.

TABLE 1

| Surfactant | Foam grade | ΣGME |
|---|---|---|
| Uncoated Control | 3* | 510,213 |
| ANTIFOAM A ™ | 2 | 762,020 |
| SMA ™ | 5** | 1,311,975 |
| PLURONIC L101 ™ | 1*** | 751,142 |
| SM70 ™ | 1**** | 794,698 |

*Approximately 1/4" foam on half of surface. Defoamer totally wetted out. Although the undipped control had good performance initially, foam was beginning to appear at the end of the test and it would have failed totally in a few more minutes.
**Defoamer does not wet out, but approximately 2" foam.
***No bubbles on surface.
****Tiny bubbles visible on wall.

Example 2

The procedure of Example 1 was used with the exceptions noted as follows:

SMA was coated on the defoamer unit in a 2% (v/v) solution using isopropyl alcohol and methylene chloride as solvents.

The blood and air flows were as follows for separate tests:
Venous line: 6 liters per minute blood flow with 0.5 liters per minute air;
Sucker bypass: 6 liters per minute blood flow into the cardiotomy port and no air flow;
Venous and Cardiotomy Flow: 3 liters per minute blood flow into venous port, 3 liters per minute blood flow into the cardiotomy port, 1.5 liters per minute air into cardiotomy port;
Filter Bypass: 6 liters per minute blood flow with 0.5 liters per minute air into Filter Bypass Port.

The blood was adjusted to 35 hematocrit and changed for each new defoamer tested. Hatteland sensitivity was five. All testing was done with nonfiltered reservoirs, maintain a blood level of 500–600 ml. All units were nonsterile. The test was run for five minutes. The results are shown in Table 2. The GME shown in Table 2 is the sum of all GMEs continuously measured over the five minute test.

TABLE 2

| Surfactant | | Venous Line | Sucker Bypass | Venous & Card. Flow | Filter Bypass |
|---|---|---|---|---|---|
| ANTIFOAM A ™ | GME | 662,063 | 733,705 | 1,506,749 | 2,000,453 |
| | Grade | 2 | 2 | 2 | 3 |
| SMA ™ | GME | 790,708 | 671,116 | 1,912,840 | Not Tested |
| | Grade | 3 | 2 | 5* | |
| L101 ™ | GME | 551,926 | 433,552 | 1,362,221 | 1,898,047 |
| | Grade | 2 | 1 | 1 | 1 |
| SM-70 ™ | GME | 880,759 | 695,163 | 1,936,163 | 2,748,522 |
| | Grade | 2 | 2 | 3 | 4 |

*With 2" foam

Example 3

The test apparatus was set up as shown in FIG. 1 using a Cobe HVRF 3700 filter/defoamer reservoir having a capacity of 3700 ml, except that saline solution was pumped at a rate of ¼ liter per minute from a graduated cylinder into the rapid prime inlet 27 of FIG. 2, and the membrane oxygenators were omitted from the circuit. The pump was stopped when the first drop of saline came through the defoamer into the reservoir, and the amount of saline emptied from the cylinder was measured as the breakthrough volume. Test units were sterilized. Breakthrough volume, i.e., the volume of saline required to "break through" the defoamer assembly into the reservoir, was tested using three different units coated with PLURONIC L101™ tested against a control unit coated with ANTIFOAM A™.

Results are set forth in Table 3.

TABLE 3

Breakthrough Volumes

| Unit 1. | PLURONIC L101 ™ | 35 cc |
| Unit 2. | PLURONIC L101 ™ | 60 cc |
| Unit 3. | PLURONIC L101 ™ | 30 cc |
| Unit 4. | Control Antifoam A | 375 cc |

Example 4

2,000 $cm^2$ of test material in 400 mL distilled water was extracted at 70° C. for 24 hours. The solution was tested for toxic substances. Results are set forth in Table 4.

TABLE 4

| Parameters | Results | Maximum Allowed |
| --- | --- | --- |
| Tests on Extraction Solution: | | |
| Color | Colorless | — |
| Turbidity | Clear | — |
| Protolytic Impurities | 0.00 mL 0.01 N NaOH | <0.4 mL 0.01 N NaOH |
| | 0.00 mL 0.01 N HCl | <0.8 mL 0.01 N Hcl |
| pH Change | 0.00 pH Unites | ±2 pH Units |
| Reducing Substances | 0.85 mL/20 mL | 2.0 mL/20 mL |
| Residue on Evaporation | 0.2 mg/100 mL | 50 mg/100 mL |
| UV Absorbance | 0.077 Abs Units | 0.3 Abs units |
| Aluminum, Al | <0.001 µg/mL | 1.0 µg/mL |
| Arsenic, As | <0.001 µg/mL | 0.5 µg/mL |
| Barium, Ba | 0.005 µg/mL | 0.5 µg/mL |
| Cadmium, Cd | <0.001 µg/mL | 0.1 µg/mL |
| Chromium, Cr | <0.001 µg/mL | 0.5 µg/mL |
| Copper, Cu | <0.001 µg/mL | 0.5 µg/mL |
| Lead, Pb | <0.001 µg/mL | 0.1 µg/mL |
| Mercury, Hg | <0.0001 µg/mL | 0.1 µg/mL |
| Silicon, Si | 0.079 µg/mL | 1.0 µg/mL |
| Tin, Sn | <0.001 µg/mL | 0.5 µg/mL |
| Ammonium | <2.0 µg/mL | 2.0 µg/mL |
| Chlorides | <0.4 µg/mL | 1.0 µg/mL |
| Nitrates | 0.02 µg/mL | 1.0 µg/mL |
| Nitrites | 0.007 µg/mL | 1.0 µg/mL |
| Phosphates | 0.172 µg/mL | 1.0 µg/mL |
| Sulfates | 0.125 µg/mL | 5.0 µg/mL |
| Tests on Plastic Material: | | |
| Heavy Metals | <5.0 µg/g | 5.0 µg/g |
| Residue on Ignition | 0.0 mg/g | 1.0 mg/g |

Example 5

Toxicity of PLURONIC L101™ was tested in a 2% solution in distilled water as follows:

Acute Systemic Toxicity: 0.9% sodium chloride, alcohol in saline, polyethylene glycol 400 (PEG) and cottonseed oil extracts of the test article were prepared at 70° C. for 24 hours. These extracts were injected I.V. or I.P. into groups of five mice each. Similarly, blank controls were injected into separate groups of mice. The extracts of the test article did not produce a significantly greater reaction than the blank extractant when observed for up to seven days.

Intracutaneous Toxicity: 0.9% sodium chloride, alcohol in saline, polyethylene glycol 400 (PEG) and cottonseed oil extracts of the test article were prepared at 70° C. for 24 hours. These extracts along with corresponding blanks were injected into rabbit skin and observed for local irritant effects for up to 72 hours. Extracts of the test article injected intracutaneously in rabbits did not produce a significantly greater tissue reaction than the blank extractant.

Implantation Test: A muscle implant test was conducted on the test article in rabbits. The purpose of the study was to evaluate the reaction of muscle tissue to the implanted test article over a fourteen day period. Macroscopic observation of the test article indicates a nonirritant as compared to the USP negative control implant material.

Hemolysis Test: An in-vitro test was performed using both direct contact and saline extract of the test article. Bovine blood (0.2 mL) was added to the eluates and to the negative and positive control tubes. The preparations were placed in a 37° C. water bath. After one hour, there was no significant red blood cell lysis as determined spectrophotometrically (<5%).

Cytotoxicity Test: A test of an extract of the test article was performed in culture media at 37° C. for 24 hours. Four plates which had previously been cultured with mouse fibroblast cells (L929) were fed the eluate along with negative and positive controls. Following 48 hours there was no significant cell degeneration of lysis as compared to the negative control (<50%).

As shown by the above examples and test results, it is possible, with the present invention, to create a surface for a medical device that exhibits both blood compatibility and effective defoaming capability. The embodiments described herein are merely exemplary and changes and modifications in the specifically described embodiments can be carried out by one skilled in the art without departing from the scope of the invention. All such changes and modifications are intended to be included within the scope of the invention as defined in the appended claims.

What is claimed is:

1. In an extracorporeal blood processing apparatus comprising a housing having an interior and an inlet port, said housing interior having a blood contact surface formed of a hydrophobic material, said inlet port being in fluid communication with said housing interior blood contact surface, the improvement comprising:

a coating consisting essentially of a nontoxic biocompatible liquid surface-active defoaming agent durably deposited on said housing interior blood contact surface by dissolving or dispersing in an organic solvent and applying to said blood-contact surface, said defoaming agent being not significantly water soluble and having a hydrophilic-lipophilic balance rating of about 7 or less, wherein said defoaming agent is selected from the group consisting of primary alkoxylated alcohols and block copolymers of propylene oxide and ethylene oxide, said defoaming agent having a blood defoaming screen test filter bypass foam grade of 2 or less, and wherein the extracorporeal blood processing apparatus is a blood membrane oxygenator comprising a defoamer unit.

2. The extracorporeal blood processing apparatus of claim 1 wherein the defoamer unit comprises air separation netting.

3. The extracorporeal blood processing apparatus of claim 1 wherein said defoaming agent is a block copolymer of propylene oxide and ethylene oxide.

4. The extracorporeal blood processing apparatus of claim 1, wherein said defoaming agent has a cloud point temperature less than about 37° C.

5. A method of defoaming or preventing foam formation in blood comprising contacting said blood with the housing interior blood contact surface of the extracorporeal blood processing apparatus of claim 1.

6. The method of claim 5 wherein the defoamer unit comprises air separation netting.

7. The method of claim 5 wherein said defoaming agent is a block copolymer of propylene oxide and ethylene oxide.

8. The method of claim 5 wherein said defoaming agent has a cloud point temperature less that about 37° C.

9. A method of fabricating the extracorporeal blood processing apparatus of claim 1 comprising:

(a) assembling said apparatus; and (b) durably depositing a coating consisting essentially of a nontoxic biocompatible liquid surface-active defoaming agent on said housing interior blood contact surface by dissolving or dispersing in an organic solvent and applying to said blood-contact surface, said defoaming agent being not significantly water soluble and having a hydrophilic-lipophilic balance rating of about 7 or less, wherein said defoaming agent is selected from the group consisting of primary alkoxylated alcohols and block copolymers of propylene oxide and ethylene oxide, said defoaming agent having a blood defoaming screen test filter bypass foam grade of 2 or less.

10. The method of claim 9 wherein the defoamer unit comprises air separation netting.

11. The method of claim 9 wherein said defoaming agent is a block copolymer of propylene oxide and ethylene oxide.

12. The method of claim 9 wherein said defoaming agent has a cloud point temperature less than about 37° C.

* * * * *